US008906326B2

(12) United States Patent
Aoyagi et al.

(10) Patent No.: US 8,906,326 B2
(45) Date of Patent: Dec. 9, 2014

(54) BIOCHEMICAL REACTION CASSETTE

(75) Inventors: Takaaki Aoyagi, Kawasaki (JP);
Tomoyuki Makihira, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 590 days.

(21) Appl. No.: 12/518,071

(22) PCT Filed: Dec. 20, 2007

(86) PCT No.: PCT/JP2007/075230
§ 371 (c)(1),
(2), (4) Date: Jun. 5, 2009

(87) PCT Pub. No.: WO2008/081912
PCT Pub. Date: Jul. 10, 2008

(65) Prior Publication Data
US 2011/0028353 A1 Feb. 3, 2011

(30) Foreign Application Priority Data

Dec. 28, 2006 (JP) .................. 2006-356195

(51) Int. Cl.
*G01N 21/00* (2006.01)
*G05D 7/00* (2006.01)
*G01N 33/53* (2006.01)
*G01N 33/543* (2006.01)

(52) U.S. Cl.
CPC ............ *G01N 33/5302* (2013.01); *G01N 21/00* (2013.01); *G05D 7/00* (2013.01); *G01N 33/54366* (2013.01)
USPC .......................................... 422/554; 422/110

(58) Field of Classification Search
CPC ......... C40B 60/12; B01D 11/00; C12M 1/34; C12M 3/00; C12M 1/36; C07H 21/04; G01N 21/00; G01N 33/54366; G01N 33/5302; B01L 3/5027; G05D 7/00
See application file for complete search history.

(56) References Cited

U.S. PATENT DOCUMENTS

| 5,922,604 | A | * | 7/1999 | Stapleton et al. ............... 436/46 |
| 6,448,088 | B1 | * | 9/2002 | Levine et al. ................. 436/164 |
| 6,776,965 | B2 | | 8/2004 | Wyzgol et al. |

(Continued)

FOREIGN PATENT DOCUMENTS

| CN | 1597119 A | 3/2005 |
| EP | 1 120 164 A2 | 8/2001 |

(Continued)

OTHER PUBLICATIONS

PCT International Search Report and Written Opinion of the International Searching Authority, Mailing Date Feb. 12, 2008.

(Continued)

*Primary Examiner* — Lore Jarrett
(74) *Attorney, Agent, or Firm* — Fitzpatrick, Cella, Harper and Scinto

(57) ABSTRACT

A biochemical reaction cassette having a structure for uniformizing a liquid flow in a reaction chamber with a simple additional arrangement is provided. A fluid resistive section is arranged in a channel that is constructed to include an injection port, a reaction chamber, and a discharge port. The fluid resistive section decreases the cross-sectional area of the channel to decrease the fluid resistance at ends in the width direction of the fluid resistive section and at positions remote from the injection port and the discharge port, where the flow rate is decreased.

4 Claims, 12 Drawing Sheets

(56) References Cited

U.S. PATENT DOCUMENTS

| | | | |
|---|---|---|---|
| 7,569,381 B2 | 8/2009 | Aoyagi | |
| 7,585,462 B2 * | 9/2009 | Parng | 422/417 |
| 7,931,868 B2 | 4/2011 | Blankenstein et al. | |
| 2003/0162283 A1 | 8/2003 | Kuno et al. | |
| 2004/0037739 A1 * | 2/2004 | McNeely et al. | 422/58 |
| 2004/0232074 A1 * | 11/2004 | Peters et al. | 210/634 |
| 2005/0026346 A1 * | 2/2005 | Blankenstein et al. | 438/200 |
| 2007/0004029 A1 * | 1/2007 | Aoyagi | 435/287.2 |
| 2007/0077645 A1 | 4/2007 | Aoyagi | |
| 2011/0045505 A1 * | 2/2011 | Warthoe et al. | 435/7.92 |

FOREIGN PATENT DOCUMENTS

| | | |
|---|---|---|
| EP | 1 201 304 A2 | 5/2002 |
| EP | 1 738 828 A2 | 1/2007 |
| EP | 1 762 300 A2 | 3/2007 |
| JP | 2002-243748 A | 8/2002 |
| JP | 2003-302399 A | 10/2003 |
| JP | 2003-315337 A | 11/2003 |
| JP | 2005-30906 A | 2/2005 |
| JP | 2006-322822 A | 11/2006 |
| JP | 2007-40969 A | 2/2007 |
| JP | 2007-78490 A | 3/2007 |

OTHER PUBLICATIONS

Chinese Office Action dated Feb. 29, 2012 in Chinese Application No. 200780048349.0.

European Search Report dated Jan. 2, 2012 in European Application No. 07851118.5.

European Office Action dated Jul. 31, 2012 in European Application No. 07 851 118.5.

* cited by examiner

BIOCHEMICAL REACTION CASSETTE

TECHNICAL FIELD

The present invention relates to a biochemical reaction cassette including a probe carrier such as a DNA microarray. The biochemical reaction cassette can be suitably used for examining a sample such as blood for, for example, whether a gene derived from a pathogenic microorganism is present or not and the result can be used as one factor in the determination of the subject's health condition. More specifically, the present invention relates to a structure of the biochemical reaction cassette for improving a flow of a liquid or a gas present in a reaction chamber.

BACKGROUND ART

Many methods utilizing a hybridization reaction using a probe carrier typified by a DNA microarray have been proposed as methods for rapidly and precisely determining the base sequence of a nucleic acid or detecting a target nucleic acid in a nucleic acid sample. The DNA microarray is that in which a probe including a nucleotide sequence that is complementary to a target nucleic acid is immobilized on a solid-phase such as a bead or a glass plate at a high density. In general, the detection of a target nucleic acid using the DNA microarray includes the following steps.

In the first step, a target nucleic acid is amplified by an amplification method typified by PCR. Specifically, firstly, first and second primers are added to a nucleic acid sample solution, and the mixture is subjected to a thermal cycle. The first primer specifically binds to part of the target nucleic acid, and the second primer specifically binds to part of a nucleic acid that is complementary to the target nucleic acid. The binding of the first and the second primers to a double-stranded nucleic acid containing the target nucleic acid causes amplification of the double-stranded nucleic acid containing the target nucleic acid by an extension reaction. After sufficient amplification of the double-stranded nucleic acid containing the target nucleic acid, a third primer is added to the nucleic acid sample solution, and the resulting mixture is subjected to a thermal cycle. The third primer is labeled with an enzyme, a fluorescent substance, a luminescent substance, or the like and specifically binds to part of a nucleic acid that is complementary to the target nucleic acid. The binding of the third primer to the nucleic acid that is complementary to the target nucleic acid causes amplification of the target nucleic acid labeled with an enzyme, a fluorescent substance, a luminescent substance, or the like by an extension reaction. That is, when the nucleic acid sample solution contains the target nucleic acid, the labeled target nucleic acid is generated. However, when the nucleic acid sample solution does not contain the target nucleic acid, no labeled target nucleic acid is generated.

In the second step, this nucleic acid sample solution is brought into contact with a DNA microarray for a hybridization reaction with a probe of the DNA microarray. The probe and the target nucleic acid form a hybrid when the nucleic acid sample solution contains a target nucleic acid that is complementary to the probe.

In the third step, the target nucleic acid is detected. Whether or not the probe and the target nucleic acid have formed a hybrid can be detected by means of the labeling substance of the labeled target nucleic acid. Thus, the presence or absence of a specific base sequence can be confirmed.

The DNA microarray utilizing a hybridization reaction is expected to be applied to medical diagnosis for identifying pathogenic microorganisms and to gene diagnosis for examining a patient for genetic constitution. However, in most cases, each step of amplification, hybridization, and detection of a nucleic acid is conducted by using its respective apparatuses. Consequently, the overall operation is complicated, and diagnosis hence takes a long time. In particular, in a case that a hybridization reaction is conducted on a slide glass, the probe-immobilizing surface is exposed. Accordingly, the probe may be lost or contaminated by touching the slide glass with a finger or the like. Therefore, careful handling is required. For the purpose of eliminating these problems, some biochemical reaction cassette structures in which a reaction chamber is provided with a DNA microarray so that a hybridization reaction and also a subsequent detection step can be performed in the reaction chamber have been proposed.

Japanese Patent Application Laid-Open No. 2003-302399 discloses a chamber structure for preventing air bubbles from remaining in the initial stage of filling with a liquid. Furthermore, Japanese Patent Application Laid-Open No. 2002-243748 discloses a structure for forming a uniform spread and a uniform flow of a liquid.

The reaction chambers of these biochemical reaction cassettes are usually low in height and have a flatly extended space, and the capacity thereof is small. Since the capacity of the reaction chamber is small, the amount of a liquid such as a nucleic acid sample solution used may be small. Since the height of the reaction chamber is low, a laminar flow is generated in the reaction chamber. In addition, the hybridization reaction of a target nucleic acid and a probe on a solid phase can be accelerated by agitating the nucleic acid sample solution in the reaction chamber. As the simplest way, the nucleic acid sample solution in the reaction chamber can be agitated by pushing and pulling the liquid at the injection port.

The reaction of a probe and a target nucleic acid should be uniformly conducted on a DNA microarray. Accordingly, it is necessary to decrease unevenness in the hybridization reaction by allowing fluid to uniformly flow in the reaction chamber.

The structure described in Japanese Patent Application Laid-Open No. 2003-302399 can allow a liquid to uniformly spread in a reaction chamber in the initial stage of being filled with the liquid, but the flow rate in the central portion of the reaction chamber becomes high in some cases when the liquid flows in the state that the reaction chamber is filled with the liquid.

Similarly, the structure described in Japanese Patent Application Laid-Open No. 2002-243748 causes a flow rate distribution in the reaction chamber in some cases when a liquid flows in the state that the reaction chamber is filled with the liquid.

DISCLOSURE OF THE INVENTION

It is an object of the present invention to provide a biochemical reaction cassette having a structure for uniformizing a liquid flow in a reaction chamber with a simple additional arrangement.

A biochemical reaction cassette for detecting a target substance according to a first aspect of the present invention includes a reaction chamber for bringing a sample into contact with a probe-immobilizing region for detecting a target substance; an injection port for injecting the sample into the reaction chamber; a discharge port for discharging the sample from the reaction chamber; and a fluid resistive section disposed in a channel that is constructed to includes the injection port, the reaction chamber, and the discharge port. The fluid resistive section reduces the cross-sectional area of the channel and has a structure that gives a difference in the fluid resistance in the portion where the fluid resistive section is disposed in such a manner that the fluid resistance at least one end in the width direction of the channel is lower than those in the other portions.

A biochemical reaction cassette for detecting a target nucleic acid according to a second aspect of the present invention includes a probe-immobilizing region for detecting the target nucleic acid; a reaction chamber for bringing a sample into contact with the probe-immobilizing region; an injection port for injecting the sample into the reaction chamber; and a discharge port for discharging the sample from the reaction chamber. The probe-immobilizing region is arranged in the central portion in the width direction of the reaction chamber, and the reaction chamber is constructed to include a ceiling and a bottom. The probe-immobilizing region is arranged so as to contain the central portion of the ceiling or the bottom in the width direction of the reaction chamber. The distance between the ceiling and the bottom in the portion where the probe-immobilizing region is arranged is smaller than that between the ceiling and the bottom at an end in the width direction of the reaction chamber.

A biochemical reaction cassette according to a third aspect of the present invention includes both structures according to the first and second aspects.

According to the present invention, the fluid flow can be uniformly controlled by arranging a fluid resistive section in a channel constructed to include the injection port, the reaction chamber, and the discharge port so as that the cross-sectional area of the channel is reduced. However, the flow rate is decreased at the ends in the width direction of the fluid resistive section and in portions remote from the injection port and the discharge port. Accordingly, the flow resistance is reduced for preventing the decrease in the flow rate. The flow rate can be readily controlled to be uniform by arranging the injection port and the discharge port in the central portion in the channel width direction and by decreasing fluid resistance at both ends in the channel width direction by approximately the same degrees lower than that in the central portion. In addition, the flow rate in the reaction chamber can be uniformized by preventing a decrease in the flow rate at both ends of the reaction chamber by regulating the structure of the reaction chamber so that the fluid resistance near both ends, where the flow rate is low, in the width direction of the reaction chamber is smaller than that in the central portion. The further uniform flow rate can be achieved by simultaneously adopting such a structure of the reaction chamber and the above arrangement of the fluid resistive section.

Further features of the present invention will become apparent from the following description of exemplary embodiments with reference to the attached drawings.

BEST MODES FOR CARRYING OUT THE INVENTION

Preferred embodiments according to the present invention will now be described in accordance with the accompanying drawings.

First Embodiment

Figure 1:
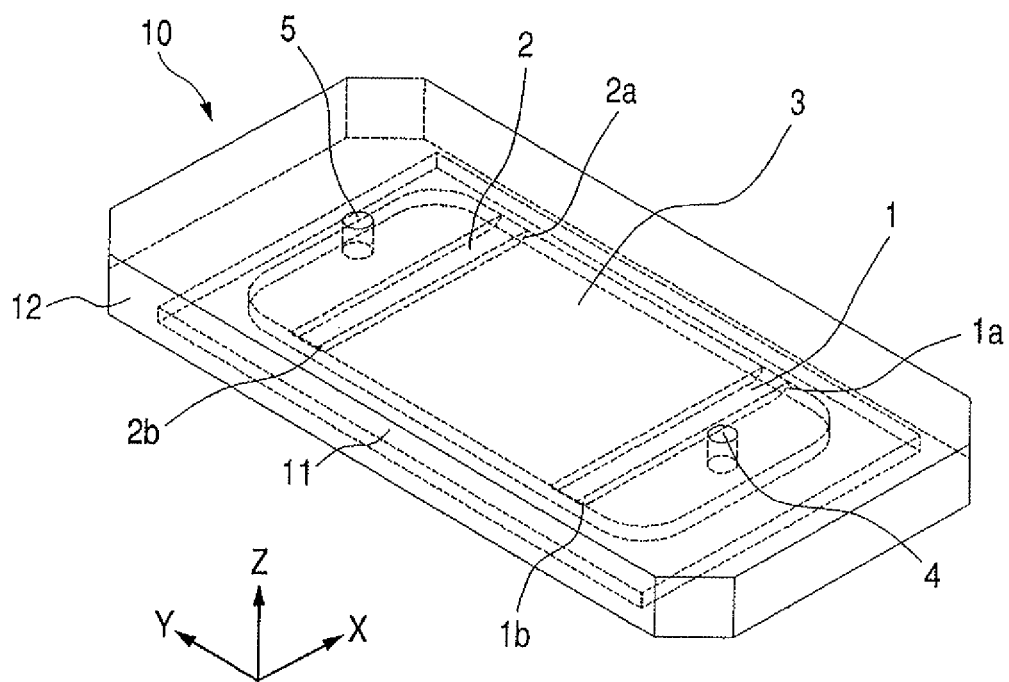
FIG. 1 is a perspective view illustrating the structure of a biochemical reaction cassette according to a first embodiment of the present invention.
Figure 2A:
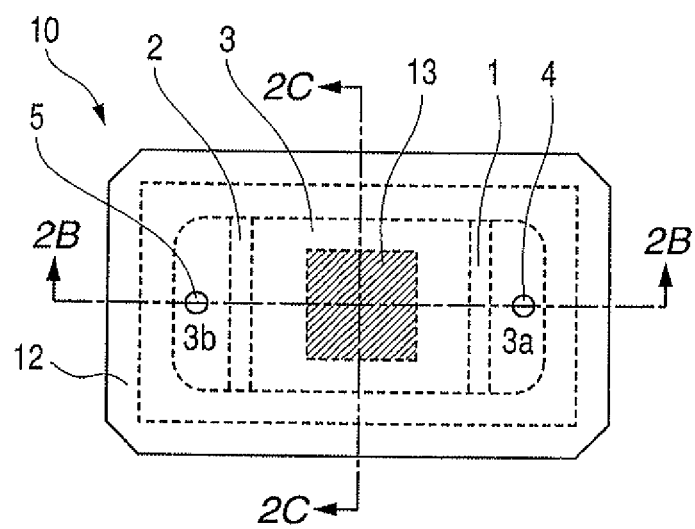
FIG. 2A is a plan view and FIGS. 2B and 2C are cross section views illustrating the structure of the biochemical reaction cassette according to the first embodiment of the present invention.
Figure 2C:
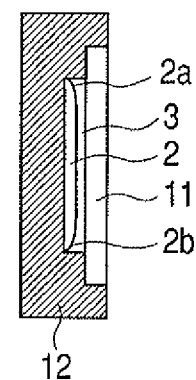
Figure 2B:
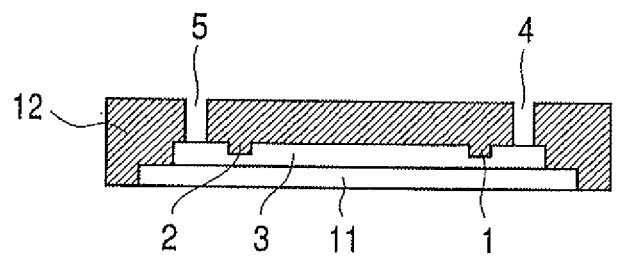

FIG. 1 is a perspective view illustrating the structure of a biochemical reaction cassette according to a first embodiment of the present invention. FIG. 2A is a plan view and FIGS. 2B and 2C are cross section views illustrating the structure of the biochemical reaction cassette according to the first embodiment of the present invention. FIG. 2B is a cross section view taken along the section 2B-2B of FIG. 2A, and FIG. 2C is a cross section view taken along the section 2C-2C.

Firstly, the structure of the cassette will be described. The cassette 10 includes a glass substrate 11 and a casing 12 that are bonded to each other. The casing is made of polycarbonate and may be formed into various shapes for bonding to the glass substrate, including the illustrated one. The material of the casing 12 is not limited to polycarbonate and may be, for example, plastic other than polycarbonate, glass, rubber, silicone, or a composite of at least two of these materials. The casing 12 is provided with a recess having a predetermined cross-sectional shape in its surface facing the glass substrate 11 so that a reaction chamber 3 is formed between the glass substrate 11 and the casing 12. Consequently, a part of the surface of the glass substrate 11 functions as the bottom surface of the reaction chamber 3. When a nucleic acid sample solution filling the reaction chamber 3 contains a target nucleic acid, the target nucleic acid reacts with the probe of a probe-immobilizing region 13 disposed on a part of the surface of the glass substrate 11. The combination of a target nucleic acid and a probe can be selected according to the purpose of detection, for example, both the target nucleic acid and the probe may be DNA. The probe-immobilizing region can be formed by using a probe carrier such as a DNA chip in which a large number of probes are arranged and immobilized on a support.

The casing 12 is provided with an injection port 4 and a discharge port 5 that connect the reaction chamber 3 and the space outside the cassette 10 through buffer regions 3a and 3b. In this embodiment, the bottom of the ceiling has a planar face in the reaction chamber 3 and the buffer regions 3a and 3b, and the height of the ceiling from the bottom is hence constant therein.

Furthermore, fluid resistive sections having protrusion members 1 and 2 are disposed adjacent to the reaction chamber 3. The protrusion members 1 and 2 are provided with small protrusions 1a, 1b, 2a, and 2b that have a small amount of protrusion at both ends. Accordingly, in the portions where the protrusion members 1 and 2 are provided, the height of the ceiling is small in the central portions and is large at both ends. A liquid is injected from the injection port 4 to the reaction chamber 3, through the buffer region 3a. The liquid passes through slot sections formed by the protrusion members 1 and 2 and is discharged from the discharge port 5 connected to the reaction chamber 3 to the outside of the cassette 10, through the buffer region 3b. That is, a channel for a liquid is formed by these portions. The protrusions may be provided to either the ceiling or the bottom or may be provided to both.

In this example, since the reaction chamber 3, the buffer regions 3a and 3b, and the protrusion members 1 and 2 are provided to the casing 12, the bottom of the reaction chamber 3 has a planar surface. However, the structure is not limited thereto. Some of or all the reaction chamber 3, the buffer regions 3a and 3b, and the protrusion members 1 and 2 may be provided to the glass substrate 11, so that bottoms of two or more of the reaction chamber 3, the buffer regions 3a and 3b, and the protrusions may not lie on the same plane.

In FIG. 1 and FIGS. 2A, 2B, and 2C, the reaction chamber has a fixed width in the channel direction (the length in the X-axis direction in FIG. 1). The widths of each portion do not necessarily the same, but can be the same from the viewpoints of not complicating the manufacturing process and of more effectively achieving a uniform flow rate in the reaction chamber.

In the example shown in FIG. 1 and FIGS. 2A, 2B, and 2C, the small protrusions 1a, 1b, 2a, and 2b have portions where protrusions are not provided. The small protrusions 1a, 1b, 2a, and 2b may each have a finite amount of the protrusion as long as the amount of the protrusion is less than that in the central portion of each of the protrusion members 1 and 2. In addition, in the cross-sectional shapes of the protrusion members 1 and 2 in the XZ-plane shown in FIG. 1, the amount of the protrusion is constant over a broad range of the central portion, but is not limited thereto and may change so that the amount is the largest at and around the center. Furthermore, the cross-sectional shapes of the protrusion members 1 and 2 in the XZ-plane shown in FIG. 1 have gradually changing portions in which the amount of the protrusion is gradually decreased toward both ends, but are not limited thereto. The protrusion amount may stepwise change from the center toward both ends. However, the shape shown in FIG. 1 and FIGS. 2A, 2B, and 2C is one of preferable examples as a structure that can uniformize the flow rate in the reaction chamber 3, in particular, in the central portion of the reaction chamber 3. Furthermore, the protrusion amount of the protrusion member 1 may be different from that of the protrusion member 2 in the range that the function of the protrusion members can be achieved. In this example, two protrusion members are provided. However, the number of the protrusion member may be one or three or more.

The width direction in this embodiment is the direction of a line formed by a plane perpendicular to the fluid flow direction and the bottom of the reaction chamber. The fluid flow direction is the line 2B-2B (central axis) in FIG. 2A. In this embodiment, the center in the width direction of the channel lies on this central axis, and a probe-arranging region is disposed on the central portion and extends by a predetermined distance from the central axis toward both ends in the width direction. As illustrated, the probe-immobilizing region 13 can be disposed symmetrically in the width direction so as to have the central axis at the center. These are applied to each embodiment described below.

The fluid resistive section is disposed at a position so that a suitable fluid flow is formed in the reaction chamber. The fluid resistive section can be disposed adjacent to the reaction chamber. That is, the fluid resistive section partially constituting the reaction chamber can directly affect the fluid in the reaction chamber to achieve good effectiveness. For example, as the structure shown in FIG. 1, the fluid resistive section can be disposed at the upstream side of the reaction chamber and extend from end to end across the width.

The fluid resistive section may be disposed in the upstream or the downstream of the probe-immobilizing region in the liquid flow direction. Preferably, the fluid resistive section is disposed at least in the upstream of the probe-immobilizing region. The term "liquid flow direction" includes the flow direction of a washing solution as well as the flow direction of a liquid sample. Therefore, with reference to the structure shown in FIG. 1, a structure employing either 1 or 2 or both can be selected depending on the purpose of the usage of the cassette.

Now, a process until the detection of a target nucleic acid by using the cassette will be described. Firstly, a nucleic acid sample solution is prepared, and the target nucleic acid is amplified by the above-described method, if necessary. When the nucleic acid sample solution contains the target nucleic acid, a target nucleic acid labeled with a fluorescent substance is generated in the amplification process. The labeling substance is a fluorescent substance in the above, but may be a luminescent substance, an enzyme, or the like. The nucleic acid sample solution is injected into the reaction chamber 3 of the cassette 10 from the injection port 4 with a liquid injection unit (not shown). After that the reaction chamber 3 has been filled with the nucleic acid sample solution, the nucleic acid sample solution is heated and maintained at a high temperature for allowing a hybridization reaction of the target nucleic acid in the nucleic acid sample solution and the probe on the probe-immobilizing region 13 to progress. In this step, the nucleic acid sample solution is agitated in the reaction chamber 3 by moving the solution back and forth in order to increase the frequency with which the target nucleic acid in the nucleic acid sample solution is brought into contact with the probe on the probe-immobilizing region 13. In this step, the reaction chamber 3 needs to be always filled with the nucleic acid sample solution.

If the channel is not provided with any resistance, a nucleic acid sample solution applied for agitation from the side of the injection port 4 flows from the injection port 4 toward the discharge port 5 in a substantially straight line. Consequently, the flow rate at the central portion of the reaction chamber 3 becomes high. However, the protrusion member 1 works as resistance for allowing the nucleic acid sample solution to flow in such a manner that the solution spreads all over the buffer region 3a. Then, as a result, the pressure at the buffer region 3a is increased, and hence a pressure is uniformly applied to the slot section formed by the protrusion member 1. The nucleic acid sample solution discharged from the slot section that is formed by the protrusion member 1 is forced to have a uniform flow rate in the reaction chamber 3. However, in both ends of the flow, the side walls largely affect the flow to decrease the flow rate. Accordingly, the height of the slot sections is changed by the small protrusions 1a and 1b to be larger than that at the center. Consequently, the solution actively flows and thereby the flow rate is uniformized in the entire reaction chamber 3. After transferring the nucleic acid sample solution from the injection port 4 by an amount required for agitation, the nucleic acid sample solution is then transferred from the side of the discharge port 5. As in the transferring of the nucleic acid sample solution from the side of the injection port 4, a uniform flow rate is generated in the reaction chamber 3 by the effects of the protrusion member 2 and the small protrusions 2a and 2b. After transferring the nucleic acid sample solution from the discharge port 5 by an amount required for agitation, the nucleic acid sample solution is transferred from the injection port 4 again. Thereafter, the transferring of the solution from the discharge port 5 and from the injection port 4 is repeated to agitate the nucleic acid sample solution in the reaction chamber 3. Since a uniform flow rate is generated in the reaction chamber 3, the frequency that the target nucleic acid in the nucleic acid sample solution is brought into contact with the probe is uniform, not depending on the position in the probe-immobilizing region 13. In other words, a difference in the progress of a hybridization reaction depending on the position in the probe-immobilizing region 13 can be decreased.

In addition, the following effects are achieved. When the flow rate at both ends of the reaction chamber 3 is slow, air bubbles tend to gather at corners of the reaction chamber 3. The air bubbles are formed, for example, because that the nucleic acid sample solution cannot hold the dissolved air with increasing temperature. The gathering air bubbles at the corners grow by aggregation or expansion and may hence disturb the flow of the nucleic acid sample solution in the reaction chamber 3. However, the flow rate at both ends of the reaction chamber 3 is not decreased, because of the effects of the small protrusions 1a, 1b, 2a, and 2b. Consequently, the air bubbles are actively transferred and are prevented from remaining at the corners.

If the reaction chamber 3 is left in a state being filled with the nucleic acid sample solution or if the nucleic acid sample containing a fluorescent substance is left in the state adhering to the wall surface of the reaction chamber 3, the background noise at the time of detection is increased. Therefore, these background-causing materials need to be washed off. In the washing step, a washing solution is allowed to continuously flow from the injection port 4 for a predetermined period of time. Also in this step, as in above, a uniform flow rate is generated in the reaction chamber 3 by the effects of the protrusion member 1 and the small protrusions 1a and 1b. Since the flow rate of the washing solution is uniform, the nucleic acid sample adhering to the wall surface of the reaction chamber 3 is washed off to the same extent regardless of the position in the reaction chamber 3. The target nucleic acid that has bound to the probe may be also peeled off by the flow of the washing solution. However, even if the target nucleic acid is partly peeled off from the probe-immobilizing region, the probability ratio that the target nucleic acid is peeled off is the same at any area of the probe-immobilizing region 13 because the flow rate of the washing solution is uniform.

Therefore, a variation in fluorescence intensity in the detection with an optical system (not shown) of whether the fluorescent substance-labeled target nucleic acid is present or not can be decreased.

Furthermore, after the washing, a drying step by discharging the washing solution from the reaction chamber 3 and drying the probe-immobilizing region 13 may be conducted. In such a case, air is fed from the injection port 4 and discharged from the discharge port 5. If a liquid or a water droplet remains without being eliminated, the intensity of light emitted by the fluorescent substance is decreased at such a portion compared to that at a dried portion of the probe-immobilizing region 13. Therefore, as in the case of a liquid flow, the air is can flow in the reaction chamber 3 at a uniform flow rate by the effects of the first protrusion member 1 and the small protrusions 1a and 1b, and the liquid in the reaction chamber 3 is hence discharged to the outside of the cassette 10 by a uniform force. At this stage, since the flow rates at both ends of the reaction chamber 3 are not decreased, the liquid that tends to remain at the corners of the reaction chamber 3 can be actively discharged.

As described in the above, the flow rates of the nucleic acid sample solution and the washing solution flowing in the reaction chamber 3 are controlled to be uniform, and thereby the binding ratio of the target nucleic acid to the probe is the same at any position. Thus, the accuracy of detection can be improved. Furthermore, in the case including a drying step, the remaining of a liquid or a water droplet on the probe-immobilizing region 13 can be reduced.

In addition, the buffer regions 3a and 3b are provided. Consequently, even if the injection pressure is changed when a nucleic acid sample solution is injected from the injection port 4, the change can be absorbed by the buffer region 3a.

Furthermore, the size of each component of the biochemical reaction cassette according to this embodiment may be determined depending on the purpose of the usage of the cassette, for example, so that the analysis using a small amount of a sample can be performed. This is applied to each embodiment described below.

Furthermore, the cassette may have a structure the probe-immobilizing region is detachable from the cassette. This is applied to each embodiment described below.

Second Embodiment

Figure 3:
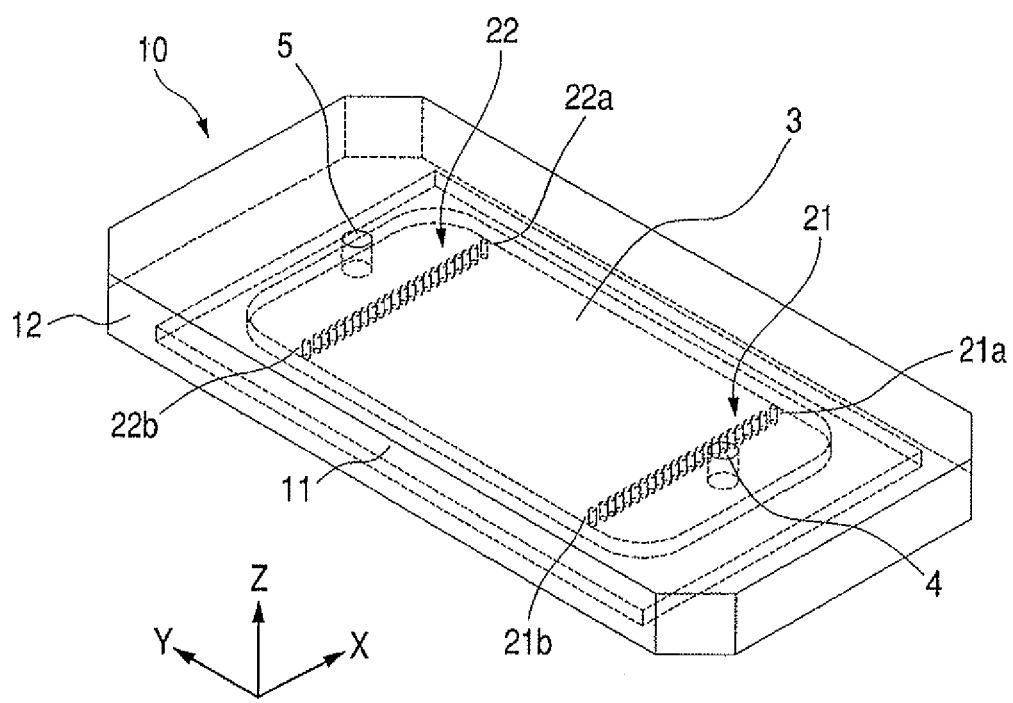
FIG. 3 is a perspective view illustrating the structure of a biochemical reaction cassette according to a second embodiment of the present invention.
Figure 4A:
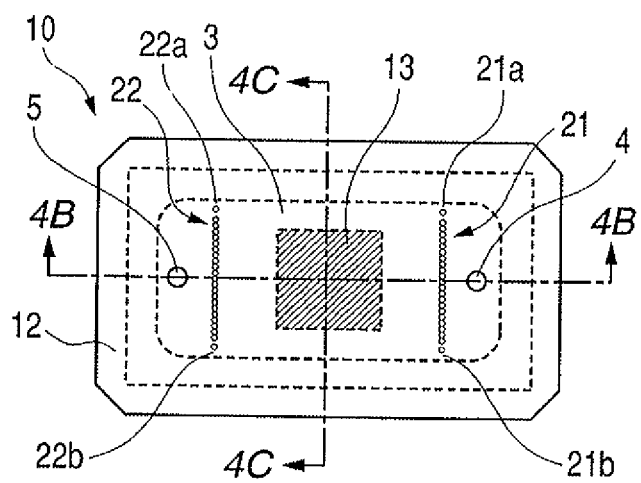
FIG. 4A is a plan view and FIGS. 4B and 4C are cross section views illustrating the structure of the biochemical reaction cassette according to the second embodiment of the present invention.
Figure 4C:
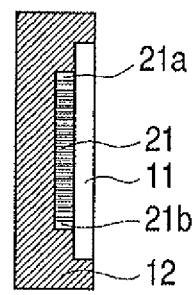
Figure 4B:
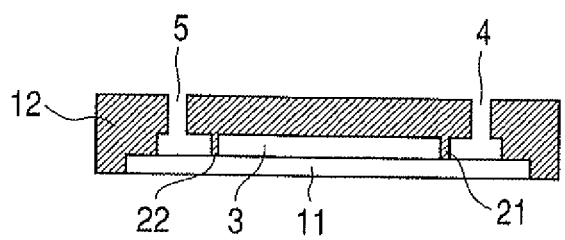

FIG. 3 is a perspective view illustrating the structure of a biochemical reaction cassette according to a second embodiment of the present invention. FIG. 4A is a plan view and FIGS. 4B and 4C are cross section views illustrating the structure of the biochemical reaction cassette according to the second embodiment of the present invention. FIG. 4B is a cross section view taken along the section 4B-4B of FIG. 4A, and FIG. 4C is a cross section view taken along the section 4C-4C.

The structure of the cassette 10 has a structure in which pillar-shaped members 21 and 22 are employed instead of the protrusion members 1 and 2 in the first embodiment. A solution passes through gaps formed by the pillar-shaped members 21 and gaps formed by the pillar-shaped members 22. The gaps formed by the pillar-shaped members 21 are large at both ends 21a and 21b thereof. Similarly, the gaps formed by the pillar-shaped members 22 are broad at both ends 22a and 22b thereof. In this example, each size of the gaps formed by pillar-shaped members 21 and 22 is different, but each diameter (width) of the pillar-shaped members 21 and 22 may be different. Furthermore, in the pillar-shaped members 21 and 22 shown in FIG. 3 and FIGS. 4A, 4B, and 4C, the columns have the same diameters are arranged in the same positions with respect to the X-direction of FIG. 3. However, the pillar-shaped members 21 and 22 may not correspond to each other in the diameters and the arrangement. Furthermore, a difference in the fluid resistance in the width direction may be achieved by controlling shapes of the pillar-shaped members. Furthermore, as in the first embodiment, a portion in which the fluid resistance is gradually or stepwise decreased may be provided in the width direction. Otherwise, this embodiment has the same structure as that of the first embodiment.

In the cassette according to this embodiment, the casing 12 is fabricated by integral molding, but the method of fabricating is not limited thereto. The pillar-shaped members 21 and 22 may be fixed by bonding, for example.

With the above-described structure, the pillar-shaped members 21 and 22 decrease the cross-sectional area of the channel to achieve effects similar to those of the protrusion members 1 and 2 in the first embodiment. In addition, effects similar to those of the small protrusions 1a, 1b, 2a, and 2b in the first embodiment are achieved by broadening the gaps formed by the pillar-shaped members in both ends 21a, 21b, 22a, and 22b. In other words, since the flow rates of the nucleic acid sample solution and the washing solution flowing in the reaction chamber 3 are uniform, the binding ratio of the target nucleic acid to the probe is the same at any position. Thus, the accuracy of detection can be improved. Furthermore, in the case including a drying step, the remaining of a liquid or a water droplet on the probe-immobilizing region 13 can be reduced.

Third Embodiment

Figure 5:
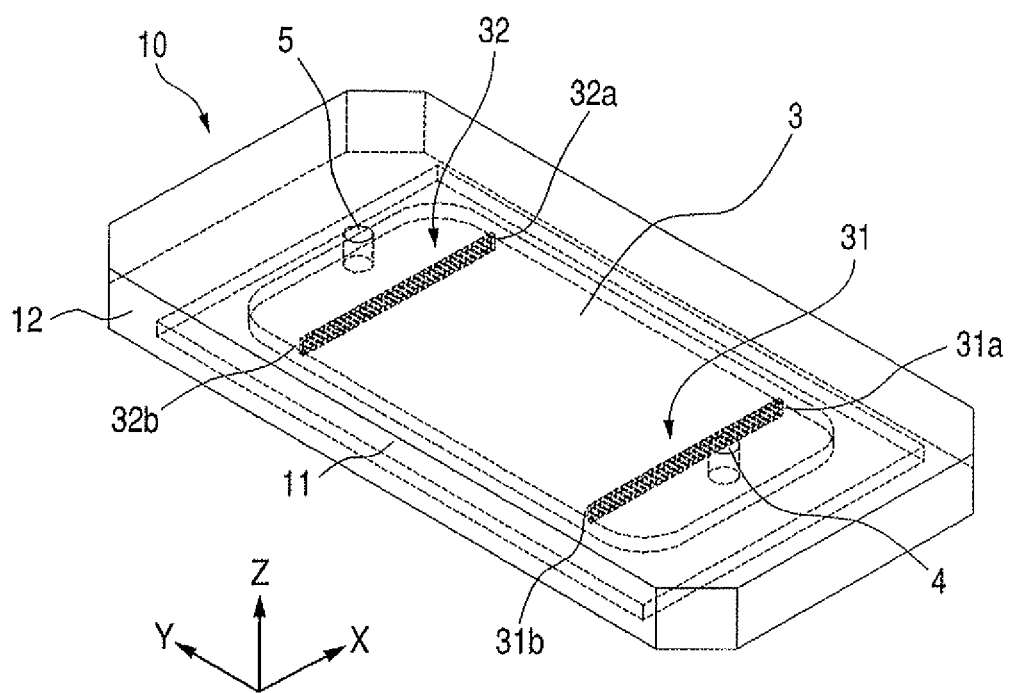
FIG. 5 is a perspective view illustrating the structure of a biochemical reaction cassette according to a third embodiment of the present invention.
Figure 6A:
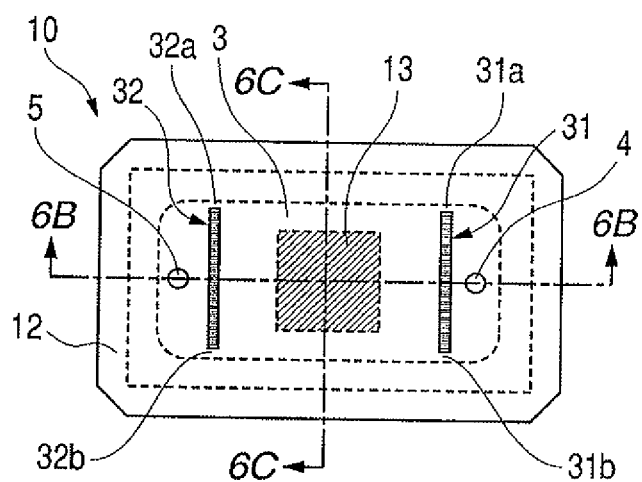
FIG. 6A is a plan view and FIGS. 6B and 6C are cross section views illustrating the structure of the biochemical reaction cassette according to the third embodiment of the present invention.
Figure 6C:
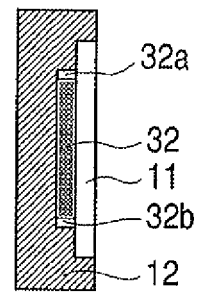
Figure 6B:
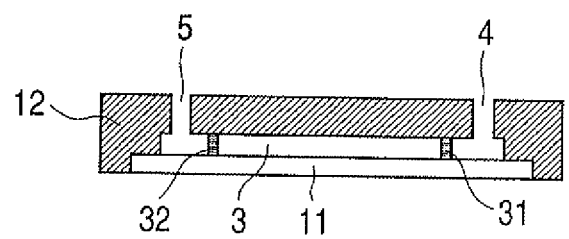

FIG. 5 is a perspective view illustrating the structure of a biochemical reaction cassette according to a third embodiment of the present invention. FIG. 6A is a plan view and FIGS. 6B and 6C are cross section views illustrating the structure of the biochemical reaction cassette according to the third embodiment of the present invention. FIG. 6B is a cross section view taken along the section 6B-6B of FIG. 6A, and FIG. 6C is a cross section view taken along the section 6C-6C.

The structure of the cassette 10 has a structure in which bulkhead members 31 and 32 are employed instead of the protrusion members 1 and 2 respectively in the first embodiment. The bulkhead members 31 and 32 are provided with a large number of through holes for passing a liquid in the Y-direction shown in FIG. 5. Small gaps are provided in both ends 31a and 31b of the bulkhead member 31 and in both ends 32a and 32b of the bulkhead member 32 to reduce fluid resistance. This example describes a structure in which the gaps are provided in both ends 31a, 31b, 32a, and 32b, but the bulkhead members may be disposed so as to extend from end to end across the width (X-direction in FIG. 5) of the reaction chamber 3 and be provided with through holes of which hole diameters or densities are increased in both ends. FIG. 5 shows an example in which the bulkhead members 31 and 32 have through holes of the same density, but it is also acceptable that the bulkhead members 31 and 32 may not have through holes of the same density. That is, a difference in the fluid resistance in the width direction can be obtained by partially controlling the sizes and/or the densities of the through holes. Furthermore, as in the first embodiment, a portion in which the fluid resistance is gradually or stepwise decreased may be provided in the width direction by partially controlling the sizes and/or the densities of the through holes. Otherwise, this embodiment has the same structure as that of the first embodiment An example of a method for manufacturing the cassette according to this embodiment will be described. The casing 12 is provided with grooves (not shown), and the bulkhead members 31 and 32 are fitted into the grooves and pinched by the casing 12 and the glass substrate 11, but the method of manufacturing is not limited thereto. Alternatively, the bulkhead members 31 and 32 may be fixed to the casing 12 by bonding, for example.

With the above-described structure, the bulkhead members 31 and 32 reduce the cross-sectional area of the channel to achieve effects similar to those of the protrusion members 1 and 2 in the first embodiment. In addition, the gaps provided in both ends 31a, 31b, 32a, and 32b achieve effects similar to those of the small protrusions 1a, 1b, 2a, and 2b in the first embodiment. In other words, since the flow rates of the nucleic acid sample solution and the washing solution flowing in the reaction chamber 3 are uniform, the binding ratio of the target nucleic acid to the probe is the same at any position. Thus, the accuracy of detection can be improved. Furthermore, in the case including a drying step, the remaining of a liquid or a water droplet on the probe-immobilizing region 13 can be reduced.

Fourth Embodiment

Figure 7:
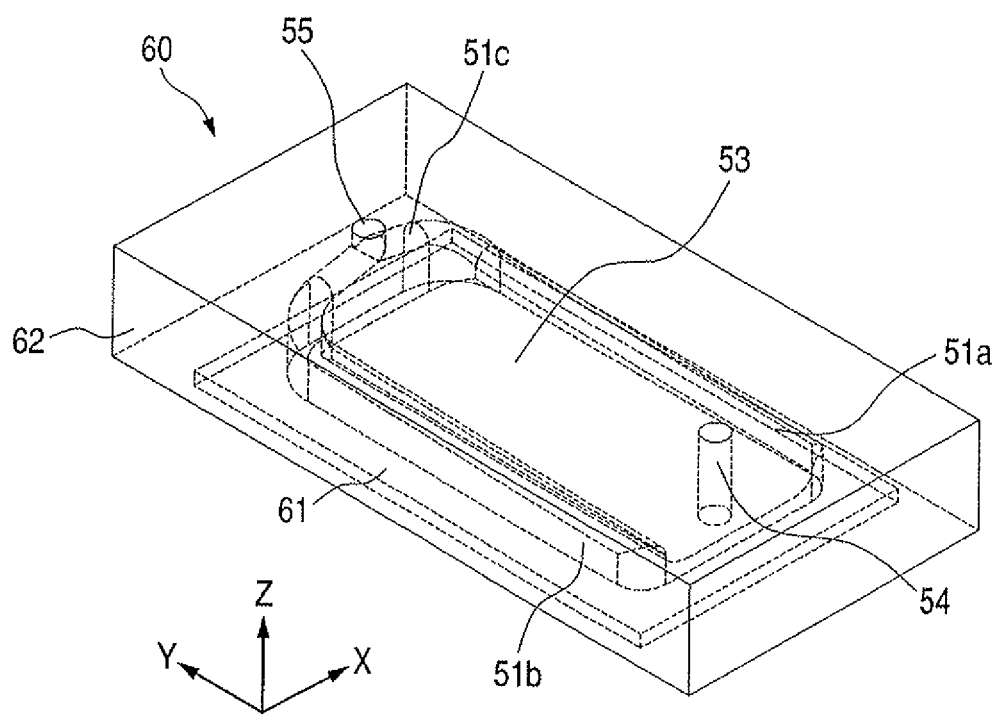
FIG. 7 is a perspective view illustrating the structure of a biochemical reaction cassette according to a fourth embodiment of the present invention.
Figure 8A:
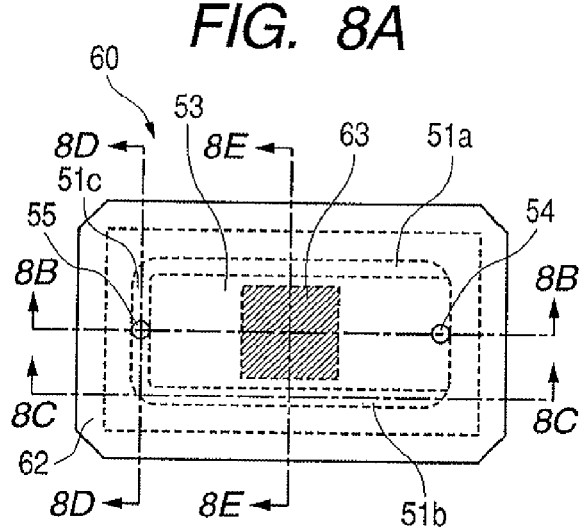
FIG. 8A is a plan view and FIGS. 8B, 8C, 8D, and 8E are cross section views illustrating the structure of the biochemical reaction cassette according to the fourth embodiment of the present invention.
Figures 8D, 8E:
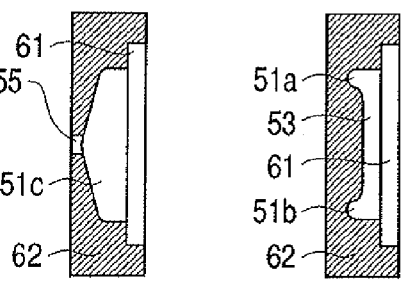
Figure 8B:
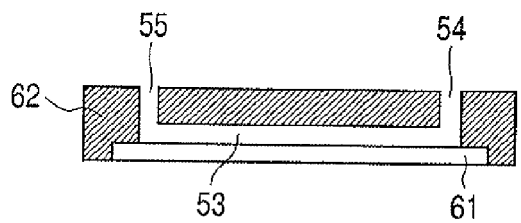
Figure 8C:
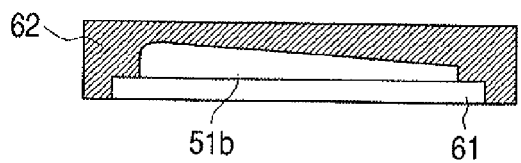

FIG. 7 is a perspective view illustrating the structure of a biochemical reaction cassette according to a fourth embodiment of the present invention. FIG. 8A is a plan view and FIGS. 8B, 8C, 8D, and 8E are cross section views illustrating the structure of the biochemical reaction cassette according to the fourth embodiment of the present invention. FIG. 8B is a cross section view taken along the section 8B-8B of FIG. 8A; FIG. 8C is a cross section view taken along the section 8C-8C; FIG. 8D is a cross section view taken along the section 8D-8D; and FIG. 8E is a cross section view taken along the section 8E-8E.

Firstly, the structure of the cassette will be described. The cassette 60 includes a glass substrate 61 and a casing 62 that are bonded to each other. The casing is made of polycarbonate and may be formed into various shapes for bonding to the glass substrate, including the illustrated one. The material of the casing 62 is not limited to polycarbonate and may be, for example, plastic other than polycarbonate, glass, rubber, silicone, or a composite of at least two of these materials. The casing 62 is provided with a recess having a predetermined cross-sectional shape in its surface facing the glass substrate 61 so that a reaction chamber 53 is formed between the glass substrate 61 and the casing 62. Consequently, a part of the surface of the glass substrate 61 functions as the bottom surface of the reaction chamber 53. When a nucleic acid sample solution filling the reaction chamber 53 contains a target nucleic acid, the target nucleic acid reacts with the probe of a probe-immobilizing region 63 disposed on a part of the surface of the glass substrate 61. The combination of a target nucleic acid and a probe can be selected according to the purpose of detection, for example, both the target nucleic acid and the probe may be DNA.

The casing 62 is provided with an injection port 54 and a discharge port 55 that connect the reaction chamber 53 and the space outside the cassette 60. In addition, the reaction chamber 53 includes grooves 51a, 51b, and 51c there surrounding. Since the height of the reaction chamber 53 is increased at the portions where the grooves 51a and 51b are provided, the fluid resistance in the central portion and that of at both ends of the reaction chamber 53 are different from each other.

The reaction chamber 53 is filled with a liquid by injecting the liquid from the injection port 54. In the initial stage, the air present in the reaction chamber 53 is driven to the grooves 51a, 51b, and 51c by injecting the liquid to the reaction chamber 53. The grooves 51a, 51b, and 51c have small slants toward the discharge port 55. Consequently, the air is gradually driven toward the discharge port 55 and discharged from the reaction chamber 53 by injecting a liquid to the reaction chamber 53, and the reaction chamber 53 is finally filled with the liquid.

Now, the flow rate distribution in the reaction chamber 53 when a nucleic acid sample solution is transferred from the injection port 54 will be described. Firstly, the height in the central portion of the reaction chamber 53 is decreased to increase the fluid resistance thereof. Thus, the fluid rate in the central portion of the reaction chamber 53 is prevented from being increased. The fluid resistance in both ends of the reaction chamber 53 is affected by not only the upper face and bottom face but also the side faces of the reaction chamber 53. Accordingly, the influences of the upper face and the bottom face of the reaction chamber 53 are decreased by the grooves 51a and 51b to uniformize the fluid resistance in the X-direction in FIG. 7. Consequently, a uniform flow rate is distributed over the entire reaction chamber 53. With the above-described effects, the agitation of a nucleic acid sample solution and the washing with a washing solution are uniformly performed on the probe-immobilizing region 63. Therefore, a variation in fluorescence intensity in the detection with an optical system (not shown) of whether the fluorescent substance-labeled target nucleic acid is present or not can be decreased.

Furthermore, in the case including a drying step, effects similar to those in the first to third embodiments can be achieved. That is, as in the injection of a liquid, air injected from the injection port 54 flows at a uniform rate in the reaction chamber 53 to discharge the liquid in the reaction chamber 53 to the outside of the cassette 60 from the discharge port 55 with a uniform force due to the effects of the grooves 51a and 51b. In this step, since the flow rate at both ends of the reaction chamber 53 is not decreased, the liquid that tends to remain at the corners of the reaction chamber 53 is actively discharged. The flow resistance in the reaction chamber 53 is controlled by adjusting the height of the reaction chamber 53 alone in this example, but may be controlled by a combination of changing the height of the reaction chamber 53 and using a fluid resistive member as shown in the first to third embodiments.

As described in the above, the flow rates of a nucleic acid sample solution and a washing solution flowing in the reaction chamber 53 are controlled to be uniform. Consequently, the binding ratio of the target nucleic acid to the probe becomes uniform at any position. Thus, the accuracy of detection can be improved. Furthermore, in the case including a drying step, the remaining of a liquid or a water droplet on the probe-immobilizing region 63 can be reduced.

Fifth Embodiment

Figure 9:
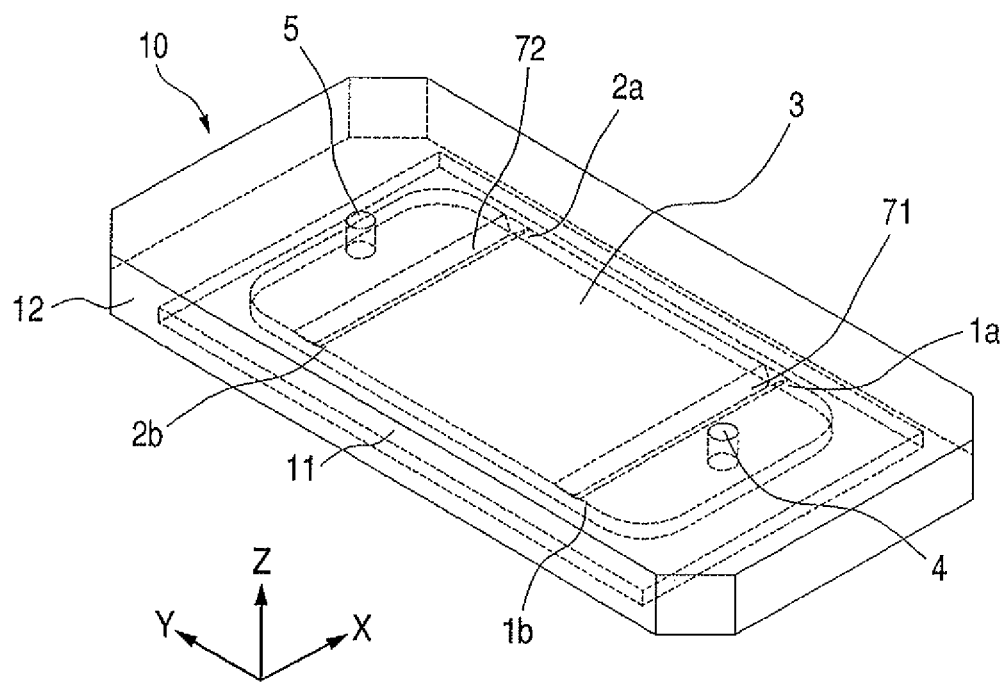
FIG. 9 is a perspective view illustrating the structure of a biochemical reaction cassette according to a fifth embodiment of the present invention.
Figure 10A:
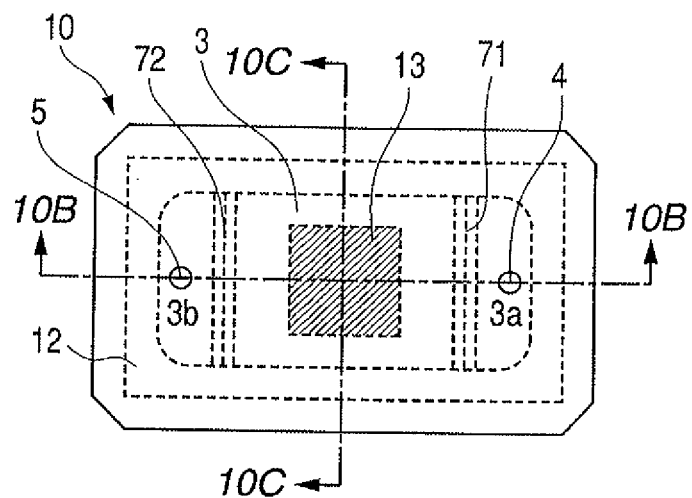
FIG. 10A is a plan view and FIGS. 10B and 10C are cross section views illustrating the structure of the biochemical reaction cassette according to the fifth embodiment of the present invention.
Figure 10C:
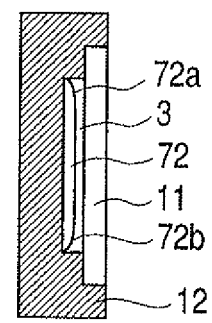
Figure 10B:
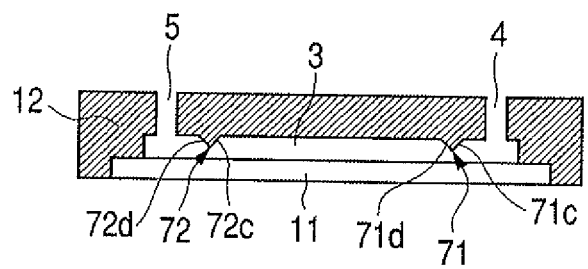

FIG. 9 is a perspective view illustrating the structure of a biochemical reaction cassette according to a fifth embodiment of the present invention. FIG. 10A is a plan view and FIGS. 10B and 10C are cross section views illustrating the structure of the biochemical reaction cassette according to the fifth embodiment of the present invention. FIG. 10B is a cross section view taken along the section 10B-10B of FIG. 10A, and FIG. 10C is a cross section view taken along the section 10C-10C of FIG. 10A.

The structure of the cassette 10 is approximately the same as that of the first embodiment. The only difference lies in protrusion members 71 and 72. Accordingly, just the effects of the protrusion members 71 and 72 will be described.

The protrusion members 71 and 72 are provided with small protrusions 71a, 71b, 72a, and 72b that have a small amount of protrusion at both ends. Consequently, the height of the ceiling is small in the central portion and is large in both ends in each of the regions where the protrusion members 71 and 72 are provided. In addition, as mostly well illustrated in FIG. 10B, the protrusion members 71 and 72 are provided with tapers 71c, 71d, 72c, and 72d.

In this example, the tapers are provided in both the upstream and the downstream of the protrusion members 71 and 72. However, only the tapers 71d and 72c that adjoin to the reaction chamber 3 may be provided. Furthermore, in the structure of this example, two protrusion members are provided. However, the number of the protrusion member may be one or three or more.

As described in the above, occurrence of swirl or turbulence in the vicinity of the protrusion members 71 and 72 due to a fluid flow in the buffer region 3a, the reaction chamber 3, and then the buffer region 3b can be decreased by providing the tapers 71c, 71d, 72c, and 72d to the protrusion members 71 and 72. The swirl and turbulence generated in the vicinity of the protrusion members 71 and 72 disturb the flow. However, the flow uniformized by the protrusion members 71 and 72 and the small protrusions 71a, 71b, 72a, and 72b can be transferred to the reaction chamber 3, without being disturbed, by the effects of the tapers 71c, 71d, 72c, and 72d.

Sixth Embodiment

Figure 11:
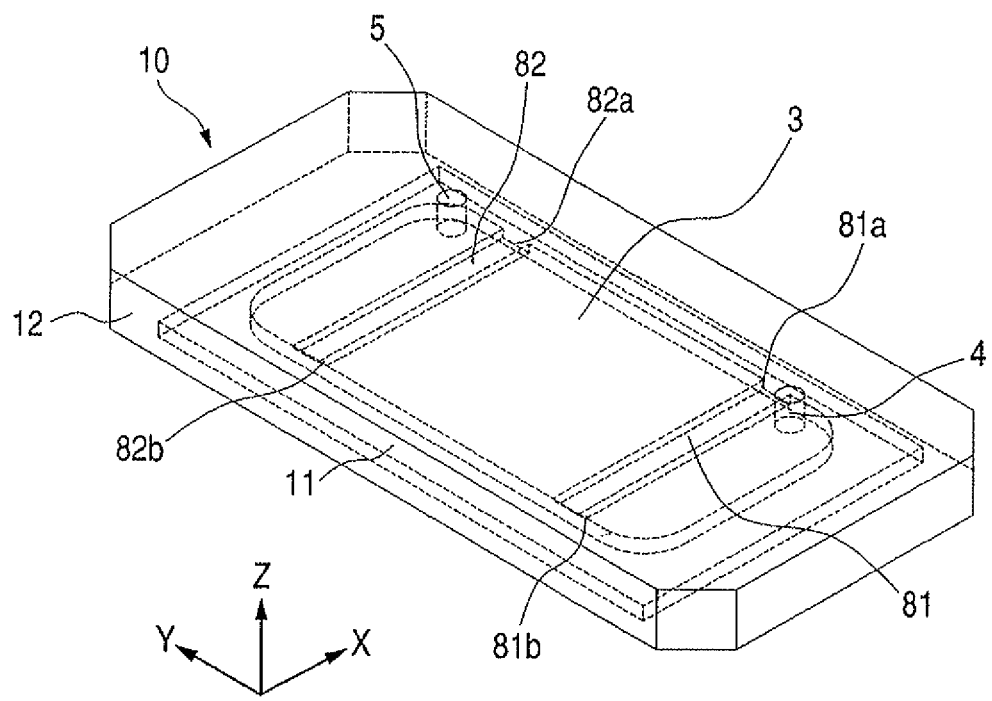
FIG. 11 is a perspective view illustrating the structure of a biochemical reaction cassette according to a sixth embodiment of the present invention.
Figure 12A:
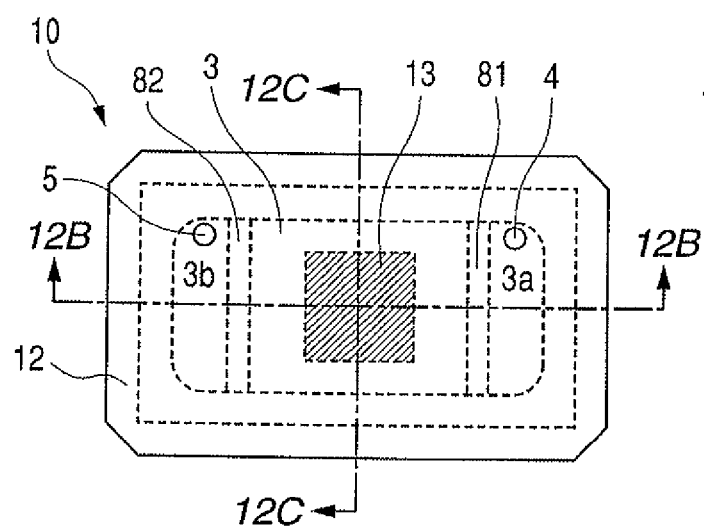
FIG. 12A is a plan view and FIGS. 12B and 12C are cross section views illustrating the structure of the biochemical reaction cassette according to the sixth embodiment of the present invention.
Figure 12C:
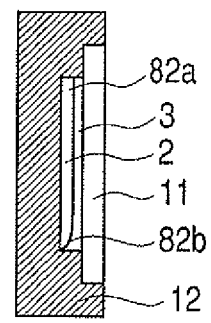
Figure 12B:
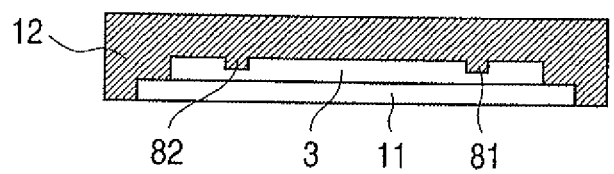

FIG. 11 is a perspective view illustrating the structure of a biochemical reaction cassette according to a sixth embodiment of the present invention. FIG. 12A is a plan view and FIGS. 12B and 12C are cross section views illustrating the structure of the biochemical reaction cassette according to the sixth embodiment of the present invention. FIG. 12B is a cross section view taken along the section 12B-12B of FIG. 12A, and FIG. 12C is a cross section view taken along the section 12C-12C of FIG. 12A.

The structure of the cassette 10 is approximately the same as that of the first embodiment. The only difference lies in the positions of the injection port 4 and the discharge port 5. Accordingly, just the shapes of the protrusion members 81 and 82 that are suitable for the positions will be described.

The injection port 4 and the discharge port 5 are disposed near a wall face of the reaction chamber 3, and the protrusion members 81 and 82 are arranged between the injection port 4 and the discharge port 5 as fluid resistance. In both ends of the protrusion members 81 and 82, the protrusion member ends 81a and 82a, which are in the vicinity of the injection port 4 and the discharge port 5, have a height that is the same as that of the central portion of the protrusion members 81 and 82. In both ends of the protrusion members 81 and 82, the protrusion member ends 81b and 82b, which are remote from the injection port 4 and the discharge port 5, have a height that is lower than that of the central portion of the protrusion members 81 and 82.

In the first embodiment, the injection port 4 and the discharge port 5 are arranged at or around the center in the width direction of the reaction chamber 3, and thereby the flow in the width direction of the reaction chamber 3 spreads to both sides. Thus, the pressure is readily moderated. However, in a structure in which the injection port 4 and the discharge port 5 are arranged near a side wall of the reaction chamber 3, the flow in the width direction of the reaction chamber 3 is generated in one side only. Consequently, the pressure is hardly moderated in such a structure. In other words, the flow rate near the injection port 4 and the discharge port 5 is hardly decreased. Therefore, if the fluid resistance of the protrusion member ends 81a and 82a is decreased, the flow rate at the protrusion member ends 81a and 82a is increased. Consequently, the flow rate in the reaction chamber 3 cannot be controlled to be uniform. Accordingly, the height of the protrusion member ends 81a and 82a is adjusted to be the same as that of the central portion of the protrusion members 81 and 82 to prevent the flow rate in the portions of the protrusion member ends 81a and 82a from increasing.

In this example, the height of the protrusion member ends 81a and 82a are controlled to be the same as that of the central portion of the protrusion members 81 and 82, but is not limited thereto. The height of the protrusion member ends 81a and 82a can be optionally determined depending on the arrangement of the injection port 4 and the discharge port 5 and on the physical properties of the fluid and the flow rate. In this example, both the injection port 4 and the discharge port 5 are disposed at the same side, but the arrangement is not limited thereto. The injection port 4 and the discharge port 5 may be arranged on different sides from each other, or one of the injection port 4 and the discharge port 5 may be disposed in the central portion in the width direction of the reaction chamber 3.

As described in the above, also in the case in which the injection port 4 and/or the discharge port 5 is arranged in the vicinity of a side wall, the flow rate can be uniformized by regulating the height of the protrusion members 81 and 82 to control the fluid resistance in the vicinity of the injection port 4 and/or the discharge port 5.

The present invention is not limited to the above embodiments and various changes and modifications can be made within the spirit and scope of the present invention. Therefore to apprise the public of the scope of the present invention, the following claims are made.

This application claims the benefit of Japanese Patent Application No. 2006-356195, filed Dec. 28, 2006, which is hereby incorporated by reference in its entirety.

The invention claimed is:

1. A biochemical reaction cassette for detecting a target substance, comprising:
   a housing having an injection port and a discharge port;
   a substrate; and
   a reaction chamber formed of the housing and the substrate,
   wherein the injection port and the discharge port are connected to the reaction chamber,
   wherein the housing member has a protrusion member, and
   wherein a region in which the amount of protrusion is decreased is provided at each end of the protrusion member so that fluid resistance at both ends of the reaction chamber in its width direction is smaller than in a central portion of the reaction chamber.

2. The biochemical reaction cassette according to claim 1, wherein the injection port is disposed near a wall face of the reaction chamber.

3. The biochemical reaction cassette according to claim 1, wherein the protrusion member has a tapered shape.

4. The biochemical reaction cassette according to claim 1, wherein the target substance is a target nucleic acid and the substrate has a probe-DNA for detecting the target nucleic acid.

* * * * *